(12) United States Patent
Takahashi

(10) Patent No.: US 7,570,792 B2
(45) Date of Patent: Aug. 4, 2009

(54) IMAGE PROCESSING APPARATUS AND CONTROL METHOD AND PROGRAM THEREFOR

(75) Inventor: Naoto Takahashi, Utsunomiya (JP)

(73) Assignee: Canon Kabushiki Kaisha, Tokyo (JP)

( * ) Notice: Subject to any disclaimer, the term of this patent is extended or adjusted under 35 U.S.C. 154(b) by 668 days.

(21) Appl. No.: 11/045,283

(22) Filed: Jan. 31, 2005

(65) Prior Publication Data

US 2005/0169534 A1 Aug. 4, 2005

(30) Foreign Application Priority Data

Feb. 4, 2004 (JP) ............................. 2004-028532

(51) Int. Cl.
*G06K 9/00* (2006.01)
(52) U.S. Cl. ............. 382/132; 250/363.01; 250/370.09
(58) Field of Classification Search ................ 382/132, 382/128–131; 250/370.09, 363.1; 378/147
See application file for complete search history.

(56) References Cited

U.S. PATENT DOCUMENTS

| 4,967,079 A | * | 10/1990 | Shimura | 250/586 |
| 4,970,393 A | * | 11/1990 | Funahashi | 250/587 |
| 5,091,970 A | * | 2/1992 | Takeo | 385/48 |
| 5,828,775 A | * | 10/1998 | Takeo et al. | 382/132 |
| 5,901,240 A | * | 5/1999 | Luo et al. | 382/132 |
| 5,901,249 A | * | 5/1999 | Ito | 382/239 |
| 5,999,638 A | * | 12/1999 | Takeo et al. | 382/132 |
| 6,052,111 A | * | 4/2000 | Shimura | 345/589 |
| 6,061,465 A | * | 5/2000 | Nakajima | 382/132 |
| 6,212,291 B1 | * | 4/2001 | Wang et al. | 382/132 |
| 6,317,510 B1 | * | 11/2001 | Murakami | 382/132 |
| 6,594,379 B1 | * | 7/2003 | Ito | 382/132 |
| 7,142,705 B2 | * | 11/2006 | Inoue et al. | 382/132 |
| 2001/0046312 A1 | * | 11/2001 | Murakami | 382/128 |
| 2003/0016854 A1 | * | 1/2003 | Inoue et al. | 382/132 |
| 2004/0182991 A1 | * | 9/2004 | Sugita | 250/208.1 |
| 2005/0254707 A1 | | 11/2005 | Takahashi | 382/168 |
| 2007/0019847 A1 | * | 1/2007 | Inoue et al. | 382/128 |

FOREIGN PATENT DOCUMENTS

| EP | 142706 A | * | 5/1985 |
| EP | 562644 A1 | * | 9/1993 |
| JP | 5-49143 | | 7/1993 |
| JP | 2596744 | | 1/1997 |
| JP | 10-162156 A | | 6/1998 |
| JP | 10162156 A | * | 6/1998 |

(Continued)

OTHER PUBLICATIONS

Jung et al. 'Rectangle Detection based on a Widowed Hough Transform', 2004, IEEE Computer Society, Proceedings of the Brazilian Symposium on Computer Graphics and Image Processing, pp. 1-9.*

(Continued)

*Primary Examiner*—Aaron W Carter
(74) *Attorney, Agent, or Firm*—Fitzpatrick, Cella, Harper & Scinto

(57) ABSTRACT

Information associated with the shape of an irradiation field candidate area is input from an operation panel. A second irradiation field recognition circuit performs irradiation field recognition on the basis of the information associated with the shape.

5 Claims, 7 Drawing Sheets

FOREIGN PATENT DOCUMENTS

| | | |
|---|---|---|
| JP | 11-328372 A | 11/1999 |
| JP | 2000-023953 | 1/2000 |
| JP | 2002-143135 A | 5/2002 |

OTHER PUBLICATIONS

Zhang et al., 'A New Algorithm for Real-Time Ellipse Detection', Nov. 2003, IEEE, Proceedings of the Second International Conference on Machine Learning and Cybernetics, pp. 602-607.*

Sonka M. et al., "Image Processing, Analysis and Machine Vision", PWS Publishing, XP002357373, second edition, (1998) pp. 254-259.

Jain A. K., "Fundamentals of Digital Image Processing, Passage", Prentice-Hall International, XP002357374, (1989) pp. 391-392.

Korean Office Action, 2006.

* cited by examiner

IMAGE PROCESSING APPARATUS AND CONTROL METHOD AND PROGRAM THEREFOR

FIELD OF THE INVENTION

The present invention relates to an image processing apparatus and its control method and program which extract an irradiation field area from an image taken by radiography.

BACKGROUND OF THE INVENTION

With the recent advances in digital technology, radiographic images are converted into digital image signals, and image processing is performed for the digital image signals to display the resultant images on a display device such as a CRT or print them out. In radiography, in order to suppress the influence of X-rays on the outside of a necessary area (irradiation field area) and prevent scattering from the outside of the necessary area to prevent a decrease in contrast, an irradiation field stop is generally used to limit the irradiation field to the necessary area.

In general, an irradiation field area is extracted in advance to optimize an image processing parameter by eliminating unnecessary information from an image obtained by using an irradiation field stop.

Such irradiation field stops include rectangular and circular stops, and recognition processing suited to the shapes of various irradiation fields have been proposed.

For example, as processing for recognizing a rectangular stop, the method disclosed in Japanese Pat. Publication No. 05-049143 is available.

In this method, X- and Y-axes are set along two adjacent sides of the contour of a rectangular irradiation field, and image data are added/totaled along the X-axis and Y-axis directions.

In this case, the level of the added/totaled data within the irradiation field becomes higher than that of data in any other area outside the irradiation field, to which almost no X-rays are applied. Positions on the Y-axis at which the levels of the added/totaled data in the X-axis direction become higher than a predetermined threshold TH and positions on the X-axis at which the levels of the added/totaled data in the Y-axis direction become higher than the predetermined thumbnail TH are calculated. The rectangular area surrounded by lines which are located at the calculated positions on the Y-axis and extend in the X-axis direction and lines which are located at the calculated positions on the X-axis and extend in the Y-axis direction is set as an irradiation field area.

As processing for recognizing a circular stop, the method disclosed in Japanese Pat. Laid-Open No. 11-328372 is available.

According to this method, radiographic image data are scanned in an array manner or radially to detect differential signal values. Points at which the detected differential signal values are equal to or higher than a threshold TH and pixel signal values nearer to the image center become higher are detected as contour candidate points regarded as points located on the contour of the irradiation field. Of the plurality of detected contour candidate points, two points which are farthest from each other are extracted. In this case, since the straight line connecting the two points on the circular contour, the distance between which is largest, is regarded as the diameter of the circle, a circular area having the straight line connecting the extracted two points as a diameter is set as an irradiation field area.

As a method of recognizing an irradiation field independently of the shape of the irradiation field, the method disclosed in Japanese Pat. No. 02596744 is available. In this method, a plurality of edge candidate points located on the end portions of an irradiation field are calculated from predetermined points contained in radiation on the basis of differential values along a plurality of radial directions. The area defined by locally connecting these edge candidate points with straight lines is set as an irradiation field area.

According to the method disclosed in Japanese Pat. Laid-Open No. 05-049143, since the area surrounded by straight lines at positions where added/totaled data in the two set directions, i.e., the X and Y directions, are higher in level than the predetermined threshold TH is set as an irradiation field area, an irradiation field in a linear shape such as a rectangular shape can be extracted. However, this method cannot cope with an irradiation field in a polygonal shape constituted by straight lines in a plurality of directions or in a curved shape such as a circular shape.

In contrast to this, according to the method disclosed in Japanese Pat. Laid-Open No. 11-328372, since a circle having, as a diameter, a line connecting two points, of extracted contour candidate points, which have the maximum distance is used, a circular irradiation field can be extracted. Obviously, however, this method cannot cope with irradiation fields other than circular irradiation fields.

According to the method disclosed in Japanese Pat. No. 02596744, since the area defined by locally connecting a plurality of calculated edge candidate points with straight lines is set as an irradiation field, not only a rectangular irradiation field but also a polygonal or circular irradiation field can be extracted. However, even an irradiation field whose boundary line should be formed from a curved line, such as a circular irradiation field, is locally approximated by straight lines, and hence the irradiation field recognition result becomes a polygonal shape similar to a circular shape. That is, an irradiation field including a curved line, e.g., a circular irradiation field, can be recognized to some degree by polygonal approximation, but a curved shape cannot be extracted with high precision.

As described above, according to the prior art, the recognition precision is low in the recognition of irradiation field fields having different shapes.

SUMMARY OF THE INVENTION

The present invention has been made in consideration of the above problem, and has as its object to provide an image processing apparatus and its control method and program which suppress a deterioration in recognition precision in the recognition of irradiation fields having different shapes.

According the present invention, the foregoing object is attained by providing an image processing apparatus which extracts an irradiation field area in an image taken by radiography, comprising:

input means for inputting information associated with a shape of an irradiation field candidate area; and second irradiation field recognition means for performing irradiation field recognition on the basis of the information associated with the shape.

According the present invention, the foregoing object is attained by providing an image processing apparatus which extracts an irradiation field area in an image taken by radiography, comprising:

first irradiation field recognition means for extracting an irradiation field candidate area in the image;

shape analysis means for calculating a feature amount associated with a shape of the irradiation field candidate area extracted by the first irradiation field recognition means and discriminating the shape of the irradiation field candidate area on the basis of the feature amount; and second irradiation field recognition means for performing irradiation field recognition on the basis of information associated with the shape discriminated by the shape analysis means.

In a preferred embodiment, the first irradiation field recognition means extracts a plurality of irradiation field end candidate points regarded as located at end portions of an irradiation field, and extracts an area surrounded by the plurality of irradiation field end candidate points as an irradiation field candidate area.

In a preferred embodiment, the shape analysis means calculates at least one of a squareness and a circularity as a feature amount associated with the shape of the irradiation field candidate area extracted by the first irradiation field recognition means.

In a preferred embodiment, the second irradiation field recognition means changes an irradiation field recognition method on the basis of the information associated with the shape.

In a preferred embodiment, the second irradiation field recognition means executes irradiation field recognition for circles when the information associated with the shape indicates a circle, and executes irradiation field recognition for rectangles when the information associated with the shape indicates a rectangle.

In a preferred embodiment, the second irradiation field recognition means extracts a plurality of irradiation field end candidate points regarded as located at end portions of an irradiation field, and determines the irradiation field area by applying a curved line to the plurality of irradiation field end candidate points when the information associated with the shape indicates a circle.

In a preferred embodiment, the second irradiation field recognition means extracts a plurality of irradiation field end candidate points regarded as located at end portions of an irradiation field, and determines the irradiation field area by applying straight lines to the plurality of irradiation field end candidate points when the information associated with the shape indicates a rectangle.

In a preferred embodiment, the second irradiation field recognition means changes an irradiation field recognition method on the basis of the information associated with the shape.

In a preferred embodiment, the second irradiation field recognition means executes irradiation field recognition for circles when the information associated with the shape indicates a circle, and executes irradiation field recognition for rectangles when the information associated with the shape indicates a rectangle.

In a preferred embodiment, the second irradiation field recognition means extracts a plurality of irradiation field end candidate points regarded as located at end portions of an irradiation field, and determines the irradiation field area by applying a curved line to the plurality of irradiation field end candidate points when the information associated with the shape indicates a circle.

In a preferred embodiment, the second irradiation field recognition means extracts a plurality of irradiation field end candidate points regarded as located at end portions of an irradiation field, and determines the irradiation field area by applying straight lines to the plurality of irradiation field end candidate points when the information associated with the shape indicates a rectangle.

According to the present invention, the foregoing object is attained by providing a control method for an image processing apparatus which extracts an irradiation field area in an image taken by radiography, comprising:

an input step of inputting information associated with a shape of an irradiation field candidate area; and a second irradiation field recognition step of performing irradiation field recognition on the basis of the information associated with the shape.

According to the present invention, the foregoing object is attained by providing a control method for an image processing apparatus which extracts an irradiation field area in an image taken by radiography, comprising:

a first irradiation field recognition step of extracting an irradiation field candidate area in the image;

a shape analysis step of calculating a feature amount associated with a shape of the irradiation field candidate area extracted in the first irradiation field recognition step and discriminating the shape of the irradiation field candidate area on the basis of the feature amount; and a second irradiation field recognition step of performing irradiation field recognition on the basis of information associated with the shape discriminated in the shape analysis step.

According to the present invention, the foregoing object is attained by providing a program for realizing control of an image processing apparatus which extracts an irradiation field area in an image taken by radiography, comprising:

a program code for an input step of inputting information associated with a shape of an irradiation field candidate area; and a program code for a second irradiation field recognition step of performing irradiation field recognition on the basis of the information associated with the shape.

According to the present invention, the foregoing object is attained by providing a program for control of an image processing apparatus which extracts an irradiation field area in an image taken by radiography, comprising:

a program code for a first irradiation field recognition step of extracting an irradiation field candidate area in the image;

a program code for a shape analysis step of calculating a feature amount associated with a shape of the irradiation field candidate area extracted in the first irradiation field recognition step and discriminating the shape of the irradiation field candidate area on the basis of the feature amount; and a program code for a second irradiation field recognition step of performing irradiation field recognition on the basis of information associated with the shape discriminated in the shape analysis step.

Other features and advantages of the present invention will be apparent from the following description taken in conjunction with the accompanying drawings, in which like reference characters designate the same or similar parts throughout the figures thereof.

BRIEF DESCRIPTION OF THE DRAWINGS

The accompanying drawings, which are incorporated in and constitute a part of the specification, illustrate embodiments of the invention and, together with the description, serve to explain the principles of the invention.

DETAILED DESCRIPTION OF THE PREFERRED EMBODIMENT

Preferred embodiment of the present invention will be described in detail in accordance with the accompanying drawings.

An embodiment of the present invention will be described in detail below with reference to the accompanying drawings.

Figure 1:
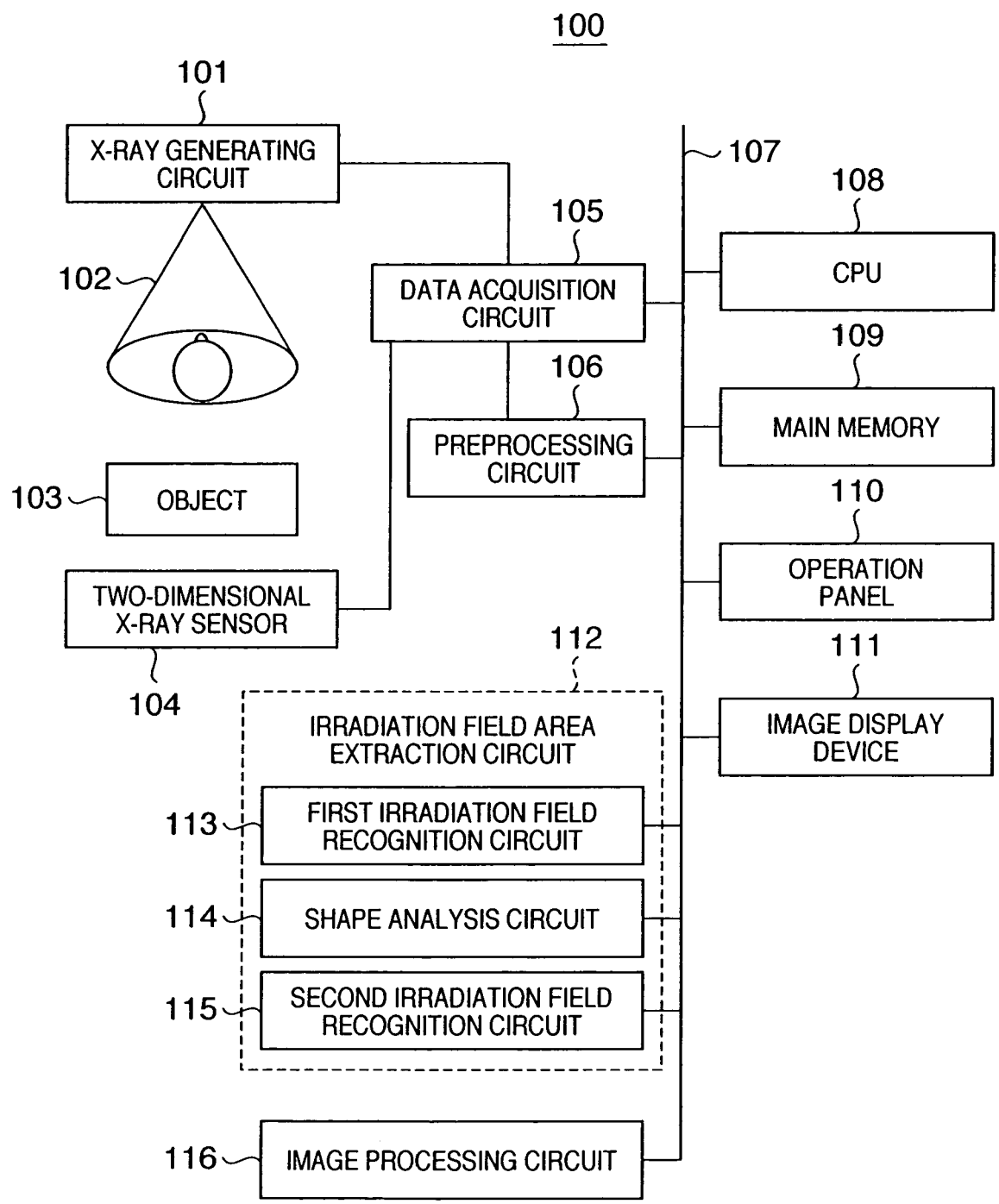
FIG. 1 is a block diagram showing the arrangement of an X-ray imaging device according to an embodiment of the present invention.

FIG. 1 is a block diagram showing the arrangement of an X-ray imaging device according to the embodiment of the present invention.

As shown in FIG. 1, an X-ray imaging device 100 has an image processing function of performing effective image processing when an X-ray image is to be output onto a filter or monitor. The X-ray imaging device 100 includes a data acquisition circuit 105, preprocessing circuit 106, CPU 108, main memory 109, operation panel 110, image display device 111, irradiation field area extraction circuit 112, and image processing circuit 116. These components are connected to each other through a CPU bus 107 so as to be capable of exchanging data.

In the X-ray imaging device 100, the data acquisition circuit 105 and preprocessing circuit 106 are connected to each other, and a two-dimensional X-ray sensor 104 and X-ray generating circuit 101 are connected to the data acquisition circuit 105. The irradiation field area extraction circuit 112 includes a first irradiation field recognition circuit 113 serving as a first irradiation field recognition means, a shape analysis circuit 114 serving as a shape analysis means, and a second irradiation field recognition circuit 115 serving as a second irradiation field recognition means. The respective circuits are connected to the CPU bus 107.

In the X-ray imaging device 100 described above, first of all, the main memory 109 stores various data necessary for processing in the CPU 108, and functions as the working memory of the CPU 108. For example, the main memory 109 is specifically a RAM, ROM, or external storage device. For example, an external storage device stores various control programs for controlling the X-ray imaging device.

The CPU 108 controls the overall operation of the apparatus in accordance with the operation of the operation panel 110 (a keyboard, pointing device, touch panel, or the like) by using the main memory 109. With this control, the X-ray imaging device 100 operates as follows.

First of all, when an instruction of capturing an image is input from a user through the operation panel 110, the CPU 108 transfers the instruction of capturing an image to the data acquisition circuit 105. Upon receiving the instruction to image, the CPU 108 executes X-ray imaging by controlling the X-ray generating circuit 101 and two-dimensional X-ray sensor 104.

In X-ray imaging, first of all, the X-ray generating circuit 101 emits an X-ray beam 102 toward an object 103 to be imaged. The X-ray beam 102 emitted from the X-ray generating circuit 101 is transmitted through the object 103 while being attenuated, and reaches the two-dimensional X-ray sensor 104. The two-dimensional X-ray sensor 104 then outputs an X-ray image signal. In this embodiment, the object 103 is assumed to be a human body. That is, the X-ray image output from the two-dimensional X-ray sensor 104 is a human body image.

The data acquisition circuit 105 converts the X-ray image signal output from the two-dimensional X-ray sensor 104 into a predetermined digital signal and supplies it as X-ray image data to the preprocessing circuit 106. The preprocessing circuit 106 performs preprocessing such as offset correction processing or gain correction processing for the signal (X-ray image data) from the data acquisition circuit 105. The X-ray image data having undergone the preprocessing in the preprocessing circuit 106 is transferred as original image data to the main memory 109 and irradiation field area extraction circuit 112 through the CPU bus 107 under the control of the CPU 108.

The irradiation field area extraction circuit 112 extracts an irradiation field area by analyzing the original image to generate irradiation field area information. The image processing circuit 116 performs various kinds of image processing for the X-ray image signal of the original image on the basis of the irradiation field area information. The image processing includes, for example, calculating the histogram of pixel values within the irradiation field area on the basis of the irradiation field area information, and calculating a grayscale processing condition for making the contrast of a region of interest suitable for diagnosis processing. Grayscale processing is then performed for the original image by using the calculated grayscale processing condition.

In the irradiation field area extraction circuit 112, the first irradiation field recognition circuit 113 extracts an irradiation field candidate area in the image. The shape analysis circuit 114 calculates a feature amount associated with the shape of the irradiation field candidate area extracted by the first irradiation field recognition circuit 113, and discriminates the shape of the irradiation field candidate area on the basis of the feature amount. The second irradiation field recognition circuit 115 differently performs irradiation field recognition depending on the feature amount associated with the shape discriminated by the shape analysis circuit 114.

The operation of the X-ray imaging device according to this embodiment having the above arrangement will be described in detail with reference to FIG. 2.

Figure 2:
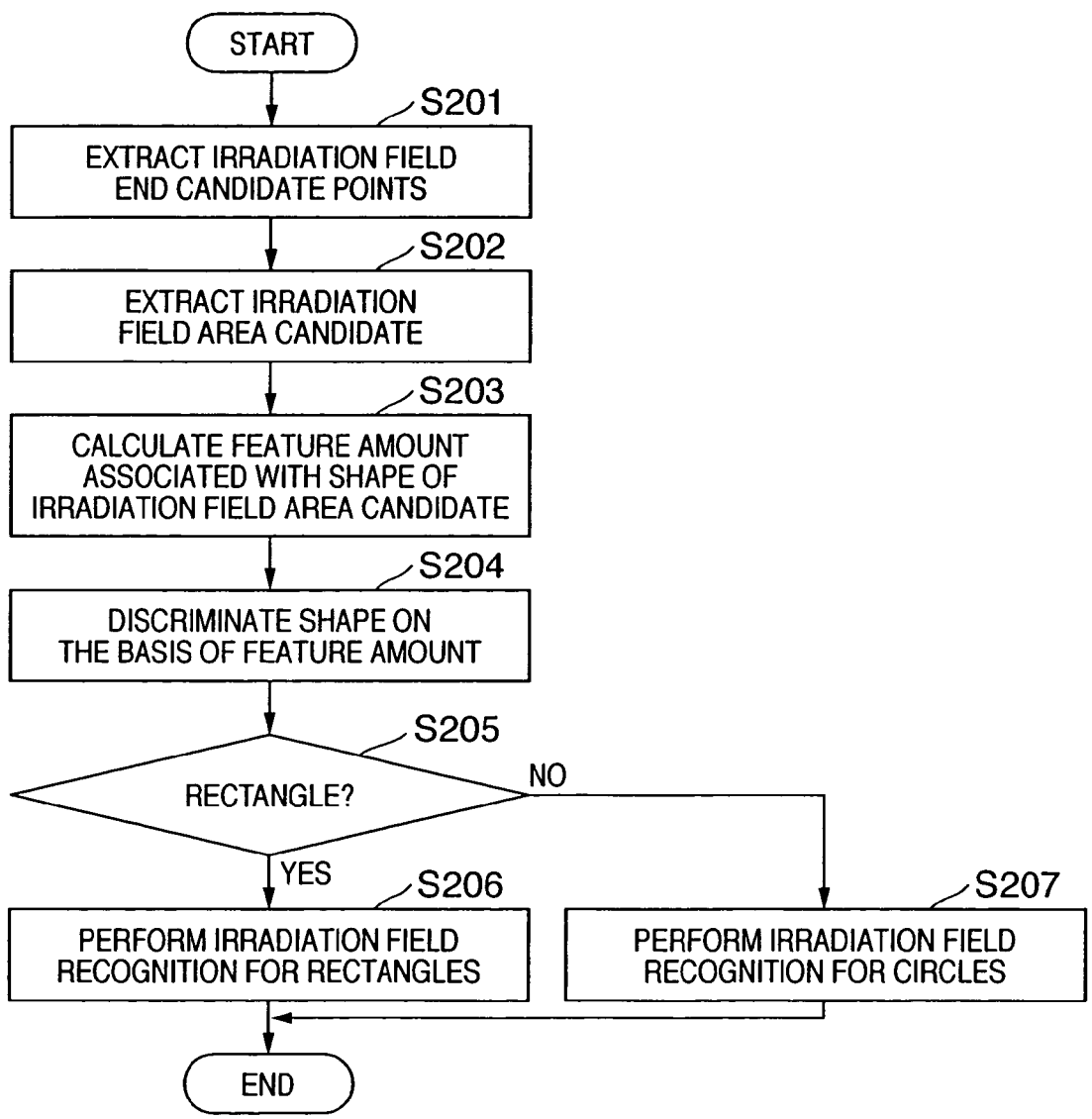
FIG. 2 is a flowchart showing the flow of processing by an irradiation field area extraction circuit according to the embodiment of the present invention.

FIG. 2 is a flowchart showing the flow of processing by the irradiation field area extraction circuit according to the embodiment of the present invention.

A portion associated with irradiation field area extraction processing will be described below with reference to the flow of processing in FIG. 2.

The original image obtained by the preprocessing circuit 106 in the above manner is transferred to the irradiation field area extraction circuit 112 through the CPU bus 107. First of all, in step S201, the first irradiation field recognition circuit 113 extracts irradiation field end candidate points as irradiation field end candidates. A method of extracting irradiation field end candidate points is not specifically limited. In this embodiment, however, the method disclosed in Japanese Pat.

Laid-Open No. 2002-143135 which has already been proposed by the present inventor is used.

According to this method, an irradiation field end likelihood is scored in accordance with the pattern of the pixel values of a pixel of interest and neighboring pixels. The gradient value of each pixel is then weighted according to the score so as to obtain a feature amount. In this case, upper, lower, left, and right patterns are separately set, and a point exhibiting a maximum feature amount which is equal to or more than a threshold th is extracted for each line.

When, for example, an upper end is to be detected, a feature point is detected for each line in the vertical direction. If there is no point exhibiting a feature amount equal to or more than the threshold th on a line, no point is extracted. It suffices if a combination of feature points extracted in the four directions, i.e., up, down, left, and right, is extracted as an irradiation field end candidate point. In this case, the threshold th may be determined empirically.

Figure 3:
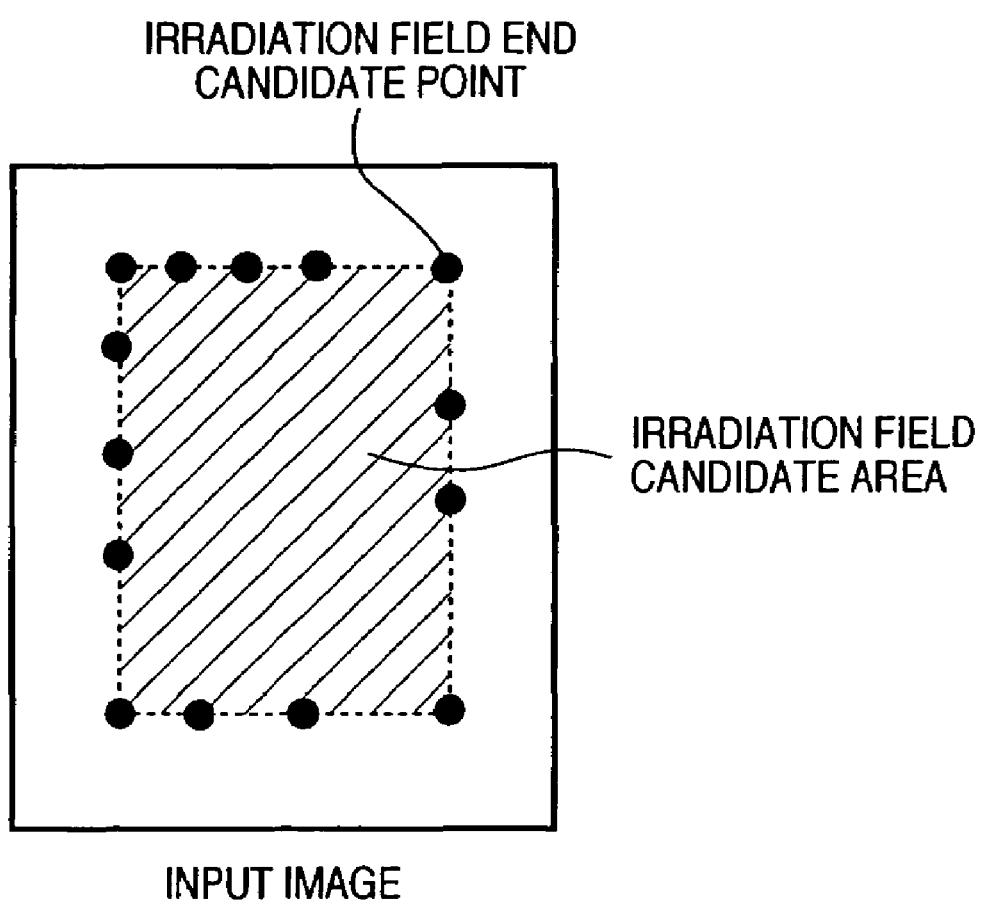
FIG. 3 is a view showing the processing result obtained by a first irradiation field recognition circuit according to the embodiment of the present invention.

In step S202, the first irradiation field recognition circuit 113 extracts an irradiation field candidate area as an irradiation field candidate in the image. In this embodiment, as shown in FIG. 3, the area surrounded by the boundary line obtained by connecting the adjacent irradiation field end candidate points extracted in step S201 with straight lines is extracted as an irradiation field candidate area.

Figure 4:
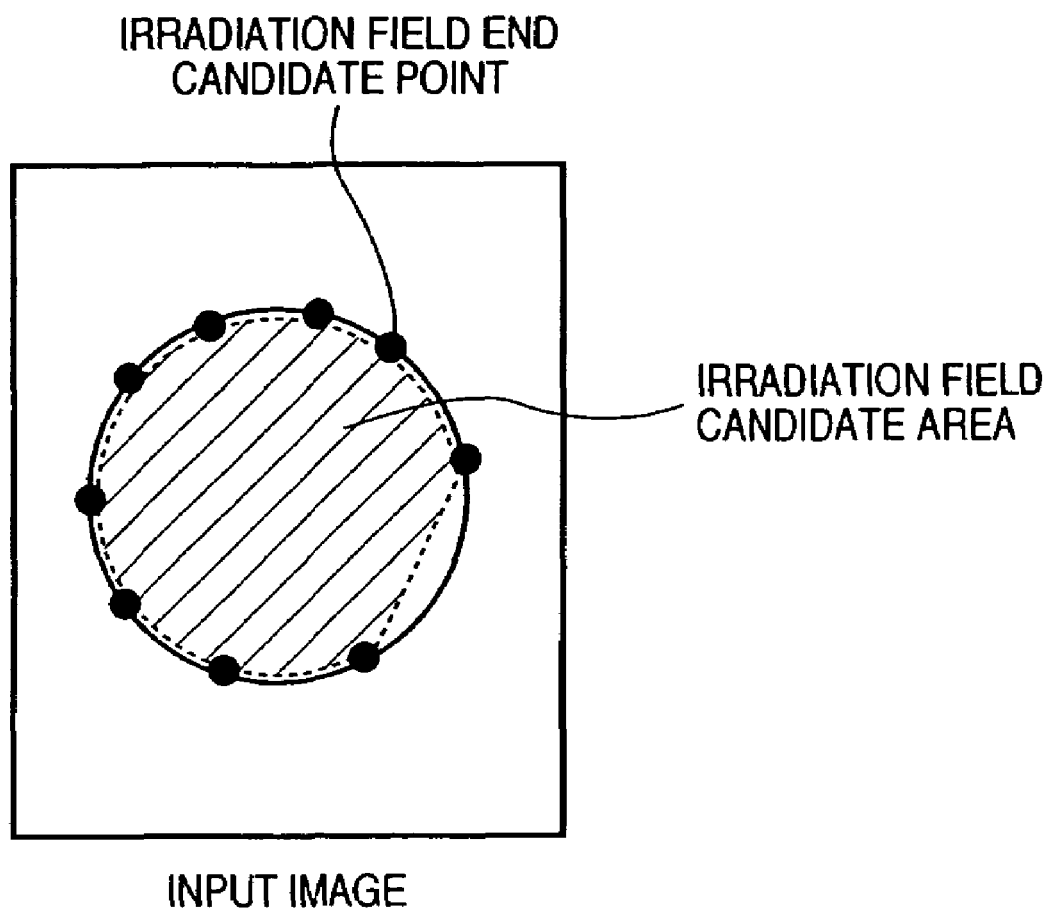
FIG. 4 is a view showing the processing result obtained by the first irradiation field recognition circuit according to the embodiment of the present invention.

In this case, in order to suppress the influence of an erroneously extracted irradiation field end candidate point, an irradiation field candidate area may be extracted upon smoothing of the boundary line. In a case of a circular irradiation field, the irradiation field candidate area extracted in this manner becomes an area approximated by a polygon, as shown in FIG. 4.

Figure 5:
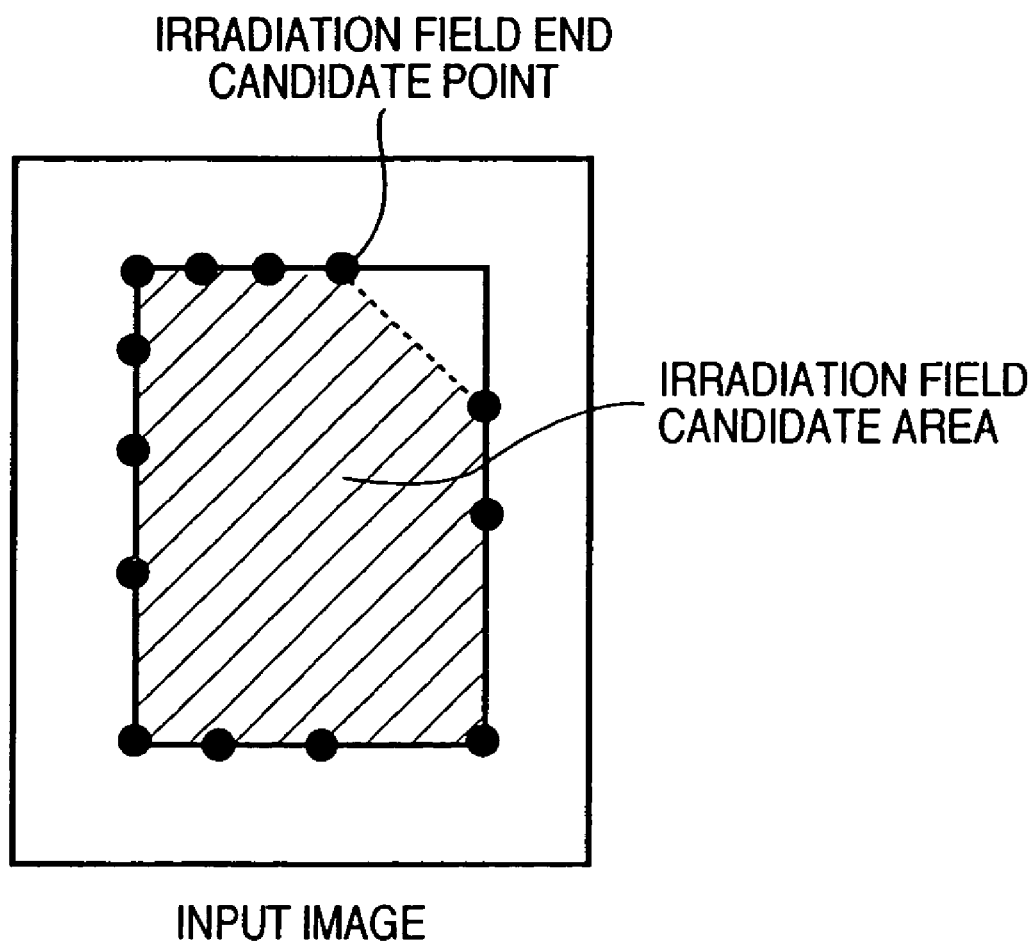
FIG. 5 is a view showing the processing result obtained by the first irradiation field recognition circuit according to the embodiment of the present invention.

In a case of a rectangular irradiation field, if no irradiation field end candidate point located at a corner of an irradiation field end can be extracted due to the influence of an X-ray shielding object or the like, an area with a loss of a corner may be extracted, as shown in FIG. 5. For this reason, although irradiation field candidate area extraction cannot be performed with high precision, an area can be roughly extracted independently of the shape of the area.

As described above, the first irradiation field recognition circuit 113 extracts a rough irradiation field area in an image. However, the present invention is not limited to this, and other irradiation field recognition methods which are not used for the shape information of an overall irradiation field may be used.

In step S203, the shape analysis circuit 114 calculates a feature amount associated with the shape of the irradiation field candidate area extracted by the first irradiation field recognition circuit 113. In this embodiment, for example, a circularity C calculated by equation (1) given below is calculated as a feature amount associated with the shape:

$$C = P^2/A \tag{1}$$

where P is the perimeter of the irradiation field candidate area, and A is the area of the irradiation field candidate area. This feature amount takes a value of $4\pi$, which is the minimum value with respect to a circle, and takes a larger value with an increase in shape complexity. It suffices to use a method other than the above method. For example, shortest distances $d_i$ (i=1, 2, ... ,n) from n pixels within the irradiation field candidate area to the boundary line may be calculated, and the circularity may be calculated according to $$C = A \bigg/ \left(\sum_{i=1}^{N} d_i\right)^2 \tag{2}$$

The feature amount calculated in the above manner reflects the complexity of the shape, and becomes larger when the target is a rectangle than when the target is a circle.

In this embodiment, a circularity is calculated. However, a feature amount associated with squareness instead of circularity may be calculated. For example, a squareness R may be calculated according to $$R = A/MER \tag{3}$$

where A is the area of the irradiation field candidate area, and MER is the area of the minimum rectangle surrounding the irradiation field candidate area. This feature amount takes a value of 1, which is the maximum value with respect to a rectangular target, and a value of $\pi/4$ with respect to a circular target. This value decreases with respect to thinner curved targets.

In addition, a feature amount associated with a shape may be calculated from a plurality of circularities or squarenesses.

In steps S204 to S207, the second irradiation field recognition circuit 115 performs different kinds of irradiation field recognition processing on the basis of information associated with the shape of the irradiation field candidate area (e.g., shape information about a rectangular, circular, or triangular area) calculated by the shape analysis circuit 114.

First of all, in step S204, the shape of the irradiation field candidate area is discriminated on the basis of the feature amount associated therewith. In this embodiment, as described above, since a circularity is calculated as a feature amount, the feature amount associated with a rectangle is relatively larger than that associated with a circle. It therefore suffices to determine the candidate area is circular if the feature amount is less than a threshold th1, and to determine the candidate area is rectangular if the feature amount is equal to or more than the threshold th1. In this case, the threshold th1 may be empirically calculated in consideration of the precision of the irradiation field candidate area extracted by the first irradiation field recognition circuit 113.

In step S205, it is determined whether or not the shape of the candidate area is rectangular. If the shape is rectangular (YES in step S205), the flow advances to step S206 to execute irradiation field recognition for rectangles.

Assume that in this embodiment, it is determined that the shape is rectangular. In this case, with regard to irradiation field end candidate points in each of the four directions, i.e., up, down, left, and right, a straight light passing through the maximum number of irradiation field candidate points is calculated.

More specifically, such straight lines may be calculated by using Hough transform. Letting $(x_i, y_i)$ be the coordinates of an extracted irradiation field end candidate point, $\rho$ be the distance from a straight line passing through the point and the origin, and $\theta$ be the angle defined by the normal to the straight line and the x-axis, the straight line is represented by $$\rho = x_i \cos\theta + y_i \sin\theta \tag{4}$$

In this case, the parameter $\rho$ and $\theta$ which determine a straight line passing through two irradiation field end candidate points on the x-y plane are given as the coordinates of the intersection of curved lines corresponding to the two irradiation field end candidate points.

Figure 6:
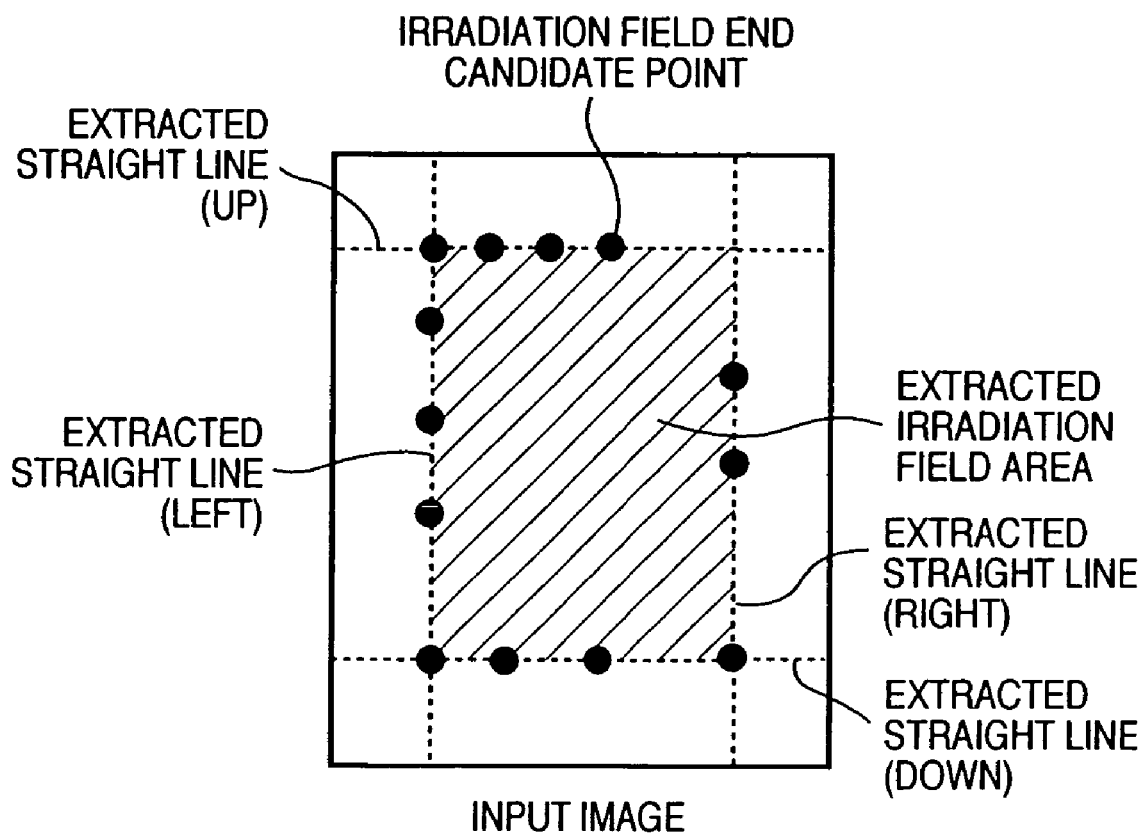
FIG. 6 is a view showing the processing result obtained by a second irradiation field recognition circuit according to the embodiment of the present invention.

On the ρ-θ plane, therefore, a straight line corresponding to a point at which the maximum number of curved lines intersect is a straight line passing through the maximum number of irradiation field end candidate points. It therefore suffices to set the area surrounded by four straight lines calculated in this manner as a rectangular irradiation field area, as shown in FIG. 6. A straight line determining method other than that described above may be used. For example, a straight line exhibiting a minimum mean square error with each irradiation field end candidate point may be calculated.

By determining an irradiation field area in the above manner, a rectangular irradiation field area can be extracted with high precision even if any feature point of a corner of an irradiation field end cannot be extracted as shown in FIG. 5 or there is an erroneously extracted feature point. In this case, irradiation field recognition for rectangles is not limited to the method described in this embodiment, and other irradiation field recognition methods specialized for rectangles may be used.

If it is determined in step S205 that the irradiation field area is not rectangular (NO in step S205), i.e., the irradiation field area is circular in this embodiment, the flow advances to step S207 to execute irradiation field recognition for circles.

In this embodiment, if it is determined that the irradiation field area is circular, a circle passing through the maximum number of points of the irradiation field end candidate points in all the directions which are extracted in step S201 is calculated.

More specifically, Hough transform is performed by using the circle equation. Letting $(x_i, y_i)$ be the coordinates of an extracted irradiation field end candidate point, $(X, Y)$ be the center coordinates of the circle, and r be the radius of the circle, the circle is represented by $$(x_1-X)^2+(y_1-Y)^2=r^2 \quad (5)$$

In this case, parameter values $(X, Y)$ which determine a circle passing through two irradiation field end candidate points on the x-y plane are given as the coordinates of the intersections of curved surfaces corresponding to the two irradiation field end candidate points.

In the three-dimensional parameter space defined by $(X,Y)$ and r, a circle corresponding to a point at which the maximum number of curved surfaces intersect is a circle passing through the maximum number of irradiation field end candidate points. It therefore suffices to extract the interior of the circle calculated in this manner as an irradiation field area. A circle determining method other than that described above may be used. For example, a circle exhibiting a minimum mean square error with each irradiation field end candidate point may be calculated. In addition, this embodiment may be applied to an ellipse instead of a circle or to a curved line for each local area.

Figure 7:
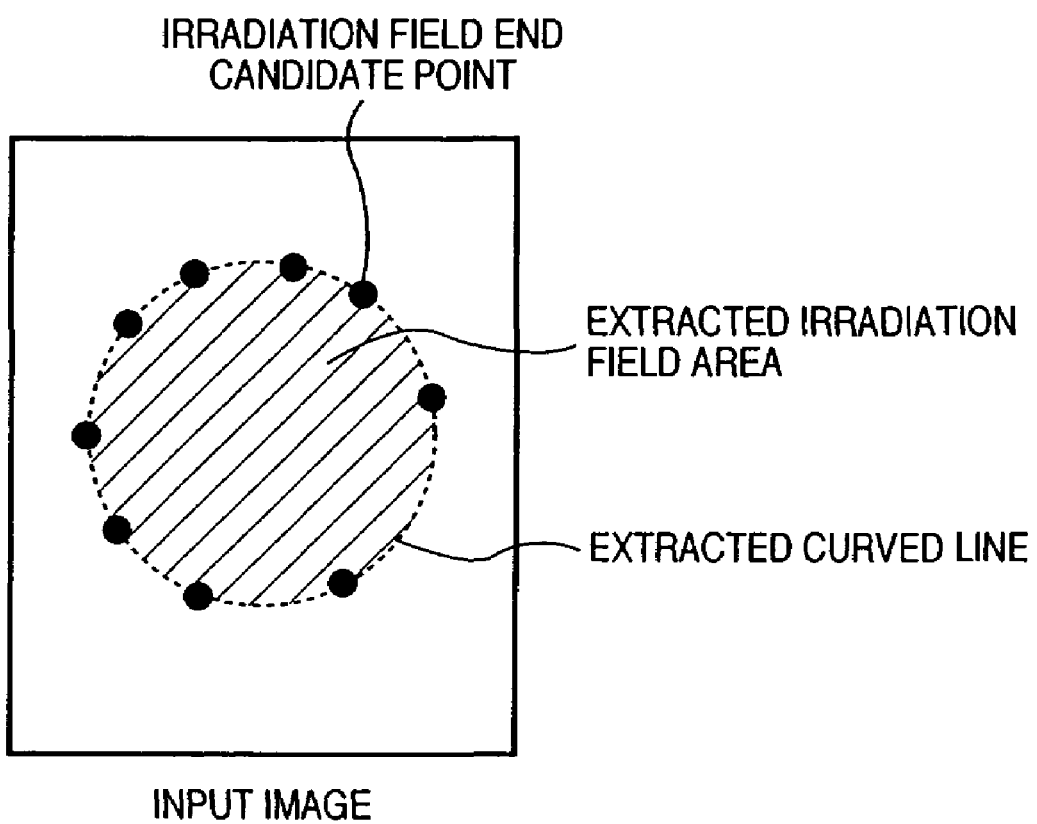
FIG. 7 is a view showing the processing result obtained by the second irradiation field recognition circuit according to the embodiment of the present invention.

By determining an irradiation field area in the above manner, since the respective irradiation field end candidate points are smoothly connected as shown in FIG. 7, high-precision irradiation field extraction can be performed as compared with the case of polygonal approximation as in FIG. 4. Even if a feature point is erroneously extracted or some feature points are lost, high-precision circle extraction can be performed. In this case, irradiation field recognition for circles is not limited to the method described in this embodiment; other irradiation field recognition methods specialized for circles may be used.

In the above description, different kinds of irradiation field recognition processing are performed on the basis of feature amounts associated with the shape of the irradiation field candidate areas calculated by the shape analysis circuit 114. However, the present invention is not limited to this. For example, information associated with the shape (e.g., shape information about a rectangle, circle, triangular, or the like) of an irradiation field candidate area is input from the operation panel 110 serving as an input means, and irradiation field recognition processing may be performed on the basis of the information.

As has been described above, according to this embodiment, since an irradiation field is recognized on the basis of information associated with the shape of the irradiation field, irradiation field recognition specialized for the shape of the irradiation field can be performed. This can prevent a deterioration in irradiation field recognition precision.

According to this embodiment, a rough irradiation field candidate area is calculated in advance, and the shape of the irradiation field is specified on the basis of the feature amount associated with the shape. This makes it possible to automatically perform irradiation field recognition specialized for the shape of the irradiation field. Therefore, a deterioration in irradiation field recognition precision can be prevented.

By recognizing the area surrounded by a plurality of irradiation field end candidate points as an irradiation field area, a rough irradiation field area can be extracted independently of the shape.

Using at least one of a squareness and a circularity as a feature of an irradiation field candidate area makes it possible to sort circles and rectangles with high precision.

By performing different kinds of irradiation field recognition for circles and rectangles in accordance with the shapes of irradiation fields, irradiation field recognition specialized for each shape can be performed. This can prevent a deterioration in irradiation field recognition precision.

Using curved lines when it is determined that an irradiation field candidate area is circular makes it possible to perform irradiation field area extraction with respect to a circular irradiation field whose boundary is a curved line. This can prevent a deterioration in irradiation field exaction precision.

Using straight lines when it is determined that an irradiation field candidate area is rectangular makes it possible to perform irradiation field area extraction with respect to a rectangular irradiation field whose boundary is comprised of straight lines. This can prevent a deterioration in irradiation field exaction precision.

In this embodiment, the shape analysis circuit 114 sorts input images into two shapes, i.e., a rectangle and a circle, and different kinds of irradiation field recognition are performed. However, the embodiment may be configured to sort input images into three or more shapes. For example, when the feature amounts of a rectangle, polygon, and circle are calculated according to equation (1), the feature amounts tend to increase in the order of the circle, polygon, and rectangle.

Images can therefore be sorted into three shapes by using a threshold TH1 for discriminating a circle and polygon and a threshold TH2 for discriminating a polygon and rectangle. It suffices to perform different kinds of irradiation field recognition with respect to the three shapes sorted in this manner. In addition, as is obvious, images can be sorted into four or more shapes by preparing a plurality of thresholds. With the above arrangement, reception processing specialized for more shapes can be performed.

Note that the present invention can be applied to an apparatus comprising a single device or to system constituted by a plurality of devices.

Furthermore, the invention can be implemented by supplying a software program, which implements the functions of the foregoing embodiments, directly or indirectly to a system or apparatus, reading the supplied program code with a computer of the system or apparatus, and then executing the program code. In this case, so long as the system or apparatus has the functions of the program, the mode of implementation need not rely upon a program.

Accordingly, since the functions of the present invention are implemented by computer, the program code installed in the computer also implements the present invention. In other words, the claims of the present invention also cover a computer program for the purpose of implementing the functions of the present invention.

In this case, so long as the system or apparatus has the functions of the program, the program may be executed in any form, such as an object code, a program executed by an interpreter, or scrip data supplied to an operating system.

Example of storage media that can be used for supplying the program are a floppy disk, a hard disk, an optical disk, a magneto-optical disk, a CD-ROM, a CD-R, a CD-RW, a magnetic tape, a non-volatile type memory card, a ROM, and a DVD (DVD-ROM and a DVD-R).

As for the method of supplying the program, a client computer can be connected to a website on the Internet using a browser of the client computer, and the computer program of the present invention or an automatically-installable compressed file of the program can be downloaded to a recording medium such as a hard disk. Further, the program of the present invention can be supplied by dividing the program code constituting the program into a plurality of files and downloading the files from different websites. In other words, a WWW (World Wide Web) server that downloads, to multiple users, the program files that implement the functions of the present invention by computer is also covered by the claims of the present invention.

It is also possible to encrypt and store the program of the present invention on a storage medium such as a CD-ROM, distribute the storage medium to users, allow users who meet certain requirements to download decryption key information from a website via the Internet, and allow these users to decrypt the encrypted program by using the key information, whereby the program is installed in the user computer.

Besides the cases where the aforementioned functions according to the embodiments are implemented by executing the read program by computer, an operating system or the like running on the computer may perform all or a part of the actual processing so that the functions of the foregoing embodiments can be implemented by this processing.

Furthermore, after the program read from the storage medium is written to a function expansion board inserted into the computer or to a memory provided in a function expansion unit connected to the computer, a CPU or the like mounted on the function expansion board or function expansion unit performs all or a part of the actual processing so that the functions of the foregoing embodiments can be implemented by this processing.

As many apparently widely different embodiments of the present invention can be made without departing from the spirit and scope thereof, it is to be understood that the invention is not limited to the specific embodiments thereof except as defined in the appended claims.

CLAIM OF PRIORITY

This application claims priority from Japanese Pat. Application No. 2004-028532 filed on Feb. 4, 2004, the entire contents of which are hereby incorporated by reference herein.

What is claimed is:

1. An image processing apparatus which extracts an irradiation field area whose overall size is a circle shape or a square shape, in an image taken by radiography, comprising:
   first irradiation field recognition means for extracting a closed curve obtained by connecting a plurality of irradiation field end candidate points as a perimeter of the irradiation field area in the image;
   shape analysis means for determining whether an overall shape of the irradiation field area extracted by said first irradiation field recognition means is a circle shape or a square shape on the basis of the perimeter or an area surrounded by the perimeter; and
   second irradiation field recognition means for extracting an overall shape of the irradiation field area as a circle shape when said shape analysis means determines that the overall shape of the irradiation filed area is the circle shape, and extracting an overall shape of the irradiation filed area is the square shape when said shape analysis means determines that the overall shape of the irradiation filed area is the square shape.

2. The apparatus according to claim 1, wherein said second irradiation field recognition means executes irradiation field recognition for circle shape when the shape analysis means determines that the overall shape of the irradiation field area is the circle shape, and executes irradiation field recognition for square shape when the shape analysis means determines that the overall shape of the irradiation field area is the square shape.

3. The apparatus according to claim 1, wherein said second irradiation field recognition means determines the overall shape of the irradiation field area as the circle shape by applying a curved line to the plurality of irradiation field end candidate points when the shape analysis means determines that the overall shape of the irradiation filed area is the circle shape.

4. A control method for an image processing apparatus which extracts an irradiation field area whose overall size is a circle shape or a square shape, in an image taken by radiography, comprising:
   a first irradiation field recognition step of extracting a closed curve obtained by connecting a plurality of irradiation field end candidate points as a perimeter of the irradiation field area in the image;
   a shape analysis step of determining whether an overall shape of the irradiation field area extracted in said first irradiation field recognition step is a circle shape or a square shape on the basis of the perimeter or an area surrounded by the perimeter; and
   an overall shape of the irradiation field area as a circle shape when it is determined said shape analysis step that the overall shape of the irradiation field area is the circle shape, and extracting an overall shape of the irradiation filed area is the square shape when it is determined in said shape analysis step that the overall shape of the irradiation filed area is the square shape, wherein said steps are performed using a computer.

5. A computer-readable storage medium, storing, in executable form, a program for control of an image processing apparatus which extracts an irradiation field area whose overall size is a circle shape or a square shape, in an image taken by radiography, the program comprising:
   a closed curve obtained by connecting a plurality of irradiation field end candidate points as a perimeter of the irradiation field area in the image;
   a program code for a shape analysis step of determining whether an overall shape of the irradiation field area extracted in the first irradiation field recognition step is a circle shape or a square shape on the basis of the perimeter or an area surrounded by the perimeter; and a program code for a second irradiation field recognition step of extracting an overall shape of the irradiation field area as a circle shape when it is determined in the shape analysis step that the overall shape of the irradiation filed area is the circle shape, and extracting an overall shape of the irradiation filed area is the square shape when it is determined in the shape analysis step that the overall shape of the irradiation filed area is the square shape.

* * * * *